(12) United States Patent
Krebs

(10) Patent No.: US 8,673,615 B2
(45) Date of Patent: Mar. 18, 2014

(54) ENHANCED PHOTOSYNTHESIS AND PHOTOCATALYSIS WATER TREATMENT/BIOMASS GROWTH PROCESS

(75) Inventor: William P. Krebs, Winnetka, IL (US)

(73) Assignee: Krebs & Sisler L.P., Winnetka, IL (US)

( * ) Notice: Subject to any disclaimer, the term of this patent is extended or adjusted under 35 U.S.C. 154(b) by 17 days.

(21) Appl. No.: 13/181,699

(22) Filed: Jul. 13, 2011

(65) Prior Publication Data

US 2012/0021494 A1    Jan. 26, 2012

Related U.S. Application Data

(60) Provisional application No. 61/367,163, filed on Jul. 23, 2010.

(51) Int. Cl.
*C12N 1/12* (2006.01)
*C12N 1/00* (2006.01)
*C12M 1/00* (2006.01)
*C02F 3/32* (2006.01)

(52) U.S. Cl.
USPC ............... 435/252.1; 435/243; 435/292.1; 435/289.1; 210/602

(58) Field of Classification Search
USPC ....................................................... 435/252.1
See application file for complete search history.

(56) References Cited

U.S. PATENT DOCUMENTS

| | | | |
|---|---|---|---|
| 3,954,615 A | 5/1976 | Shelef | |
| 3,955,318 A | 5/1976 | Hulls | |
| 5,194,161 A | 3/1993 | Heller et al. | |
| 5,449,467 A | 9/1995 | Taoda et al. | |
| 5,518,992 A * | 5/1996 | Linkous | 504/151 |
| 5,541,096 A * | 7/1996 | Nomura et al. | 435/176 |
| 6,315,904 B1 | 11/2001 | Rose et al. | |
| 6,416,993 B1 | 7/2002 | Wexler et al. | |
| 7,172,691 B2 | 2/2007 | Dunlop et al. | |
| 7,479,226 B2 | 1/2009 | Dunlop et al. | |
| 7,524,793 B2 | 4/2009 | Ortho-Gerber et al. | |
| 7,615,512 B2 | 11/2009 | Ortho-Gerber et al. | |

(Continued)

FOREIGN PATENT DOCUMENTS

| | | |
|---|---|---|
| EP | 0 634 363 A1 | 1/1995 |
| EP | 0 900 766 A1 | 10/1999 |
| WO | 2009/051479 A2 | 4/2009 |
| WO | 2010/141992 A1 | 12/2010 |

OTHER PUBLICATIONS

Benemann, "Systems and Economic Analysis of Microalgae Ponds for Conversion of CO2 to Biomass", Department of Civil Engineering, (1994) 4th Quarterly Technical Report, U.S.—Japan Joint Technical Meetings, pp. 44-51.

(Continued)

*Primary Examiner* — Ruth Davis
*Assistant Examiner* — Sheridan MacAuley
(74) *Attorney, Agent, or Firm* — Fitch, Even, Tabin & Flannery LLP

(57) ABSTRACT

A process utilizing enhanced photosynthesis and photocatalysis to purify water and/or utilize $CO_2$ on a large scale by growing biomass in reduced time and space in a closed, continuous-flow system. Added $CO_2$ and balanced nutrients combine with light to increase the growth rate of autotrophic microalgae which require $CO_2$ for growth and produce oxygen. Organic and inorganic compounds and chemical toxins are mineralized in photocatalysis using such produced oxygen, which are then absorbed (metabolized) in the microalgal biomass that is harvested.

20 Claims, 3 Drawing Sheets

(56) References Cited

U.S. PATENT DOCUMENTS

| | | |
|---|---|---|
| 7,708,884 B2 | 5/2010 | Fuchs et al. |
| 7,736,511 B2 | 6/2010 | Lugowski et al. |
| 7,744,761 B2 | 6/2010 | Constantz et al. |
| 7,968,321 B1 | 6/2011 | Green et al. |
| 7,977,076 B2 | 7/2011 | Oyler |
| 7,977,085 B2 | 7/2011 | Rispoli et al. |
| 7,981,292 B2 | 7/2011 | Limcaco |
| 7,981,647 B2 | 7/2011 | Berry et al. |
| 8,097,168 B2 | 1/2012 | Theodore et al. |
| 2005/0260553 A1 | 11/2005 | Berzin |
| 2007/0092962 A1 | 4/2007 | Sheppard |
| 2009/0215155 A1 | 8/2009 | Cloud et al. |
| 2009/0294354 A1 | 12/2009 | Theodore et al. |

OTHER PUBLICATIONS

Benemann et al., "Systems and Economic Analysis of Microalgae Ponds for Conversion of CO2 to Biomass" U.S. Department of Energy—Abstract (1996).

Rader, "Microorganisms and Their Role in the Activated-Sludge Process", U.C.L.A. Student Projects, (1998) pp. 1-19.

* cited by examiner

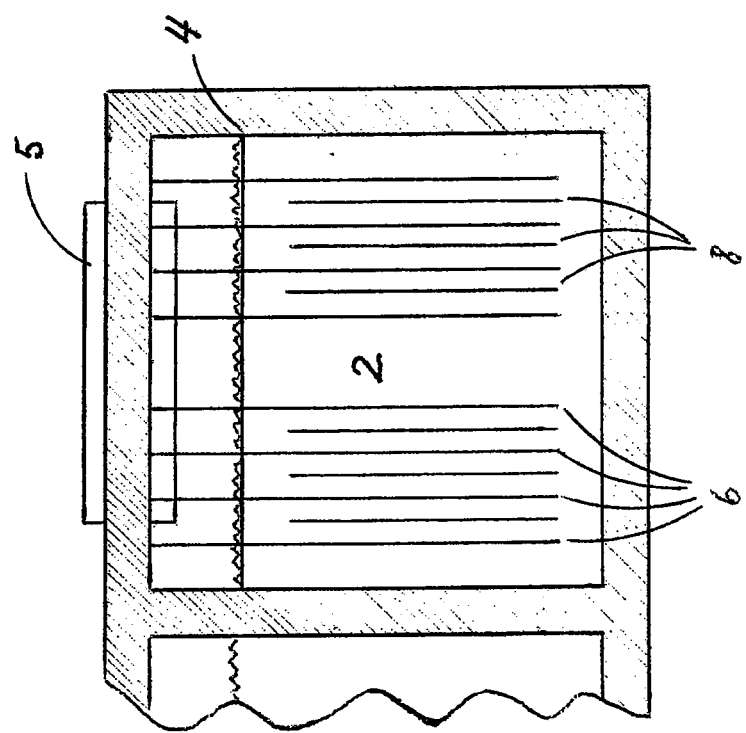

ENHANCED PHOTOSYNTHESIS AND PHOTOCATALYSIS WATER TREATMENT/BIOMASS GROWTH PROCESS

This application claims priority from U.S. Provisional Application No. 61/367,163, filed Jul. 23, 2010, the disclosure of which is incorporated herein by reference.

FIELD OF THE INVENTION

This invention relates to water treatment and the concomitant growth of biomass. More particularly, it relates to processes using enhanced photosynthesis and photocatalysis to treat water and/or dispose of $CO_2$, while at the same time growing usable biomass. Still more particularly, the invention relates to processes for treating wastewater on a large scale in continuous flow operations into which significant quantities of carbon dioxide are diffused to increase the growth rate of autotrophic microalgae.

BACKGROUND OF THE INVENTION

The following publications are of interest as explanation of the background of this invention.

American Water Works Association (AWWA) Handbook, McGraw-Hill© 1971, 1990, 1999, 2010.

"A Research Needs Assessment for the Capture, Utilization and Disposal of Carbon Dioxide from Fossil Fuel-Fired Power Plants," U.S. Department of Energy, DOE/ER-30194, July 1993.

Photocatalysis. Kirk-Othmer Encyclopedia of Chemical Technology vol. 19, 5th ed. 2006, pp. 73-106, Jean-Marie Herrmann.

Serpone, N. et al, "Heterogeneous Photocatalized Oxidation of Phenol, Cresols and Fluorophenols in $TiO_2$ Aqueous Suspensions," Photosensitive Metal-Organic Systems; American Chemical Society, Advances in Chemistry Series (ACS), pp. 281-313, 1993.

Brune, D. E. et al, "Microalgal Biomass for Greenhouse Gas Reductions: Potential for Replacement of Fossil Fuels and Animal Feeds," Journal of Environmental Engineering, pp. 1136-1144, November 2009.

"Combining Municipal Services" ©2005, www.krebsandsislerlp.com.

The large scale conversion of wastewaters and salt water to potable fresh water is being accomplished today in combinations of biological, chemical, filtration and ultraviolet radiation processes. However, the costs to reach clean water quality are so high that such methods are usually not attempted to obtain the level of potable water purity. For example, in municipal sewage wastewater reclamation, one of the largest treatment systems in the United States releases its process effluent into rivers at a published purity of only 95% to 98%, and after aerobic and anaerobic bacterial digestion, a sludge remainder of several hundred tons per day still must be hauled and disposed. Many books, papers and patents discuss the processes, technologies and the problems related to such water conditioning. A comprehensive overview is the AWWA Handbook mentioned above.

Many wastewaters (also salt water) include some or most of the nutrients needed for microalgae growth. In sewage treatment, typically a multitude of aerobic and anaerobic micro-organisms "activate" the sewage and grow biomass while their metabolism also promotes the outgassing of methane, hydrogen sulfide, ammonia and some $CO_2$. It is thought that, if such activated sewage sludge secondary treatment can be supplemented with sufficient and well-balanced nutrients, continuous lighting and large amounts of $CO_2$, and if preferred species of algae which require $CO_2$ for growth are selected, then anaerobic digestion will be suppressed with a reduction in the outgassing of methane, hydrogen sulfide and ammonia, and the autotrophic growth of cyanobacteria microalgae that require $CO_2$ should dominate.

There are many locations in the United States where large amounts of $CO_2$ are continuously available at little or no cost in mixtures of refinery offgases and the flue gases of hydrocarbon fueled power plants. However, the $CO_2$ content is usually only 5 to 15% and such gases are considered unsuitable for use in microalgae growth processes without separation to better than 90% purity. Known separation processes are expensive. One source of better than 90% purity $CO_2$ has evolved from the development of high efficiency $O_2/CO_2$ combustion for hydrocarbon and biomass fuels, as in U.S. Pat. No. 6,907,845, wherein the byproduct of steam electric generation from a condensing boiler is a stream of relatively pure $CO_2$. In this energy production concept, the costs of separating oxygen for fuel combustion and all of the costs of separating and recovering $CO_2$ are offset by virtually complete recycling of waste heat. Such improvement reduces fuel costs and can produce low cost electric power for use in an associated photosynthesis-photocatalysis water treatment system. Moreover, dry biomass produced from $CO_2$ being recycled in such a system can be used as fuel.

Photocatalysis in water treatment has the potential to destroy all or nearly all organic and inorganic compounds including toxic ones. Once mineralized, the elements are absorbed by algae in photosynthesis. By mineralized, for the purposes of this application is meant the conversion or transformation of organic and inorganic compounds by oxidation and/or reduction to mineral substances that can then be metabolized by microalgae. The above-cited references: (1) Photocatalysis: Kirk-Othmer Encyclopedia of Chemical Technology, and (2) Serpone et al, show the extent of research over many years. Although scaling up has not been promising so far, it is felt that photosynthesis and photocatalysis, acting effectively together, should be able to process the total mineral content of wastewater and other waters using the visible light spectrum. To date, it has been demonstrated that certain $TiO_2$ materials have excellent activity among photocatalysts. The recent development of a carbon-doped $TiO_2$ by Kronos International, Inc., see U.S. Pat. No. 7,615,512, which is effective to "degrade contaminants and pollutants in liquids and gases," is promising as a photocatalyst that may be able to significantly reduce the time required for the complete mineralization of chemical compounds in water treatment.

Concepts for the use of photosynthesis to dispose of $CO_2$ by growing algae in shallow open ponds have heretofore been fraught with problems, as discussed at length in a 1993 U.S. Department of Energy report referenced above. When thousands of tons of $CO_2$ need to be disposed daily, thousands of acres of land area must be utilized. One producer of the cyanobacteria Spirulina has grown this premium health food additive in Hawaii since 1985 at a rate of one ton per day in 80 acres of ponds. $CO_2$ is 27% carbon by molecular weight, and cultured Spirulina is 50% carbon. If grown at the above rate, to convert 1,000 tons of $CO_2$ per day (yielding 270 tons of carbon), 43,200 acres of ponds would be required to produce 540 tons of algae per day, assuming no $CO_2$ outgassing losses. Moreover, there are other problems, such as the diurnal and seasonal lighting constraints on growth in open ponds, variable weather limitations, $CO_2$ outgassing losses and large water losses by evaporation. It is felt that biogrowth efficiency must be increased many times to practically convert $CO_2$ to biomass at a large scale. Furthermore, there have been concerns over the presence of some species of blue-green algae in state-of-the-art water treatment. Odor and taste problems are attributed to byproducts of metabolism in the growth of some algae (see AWWA Handbook 1990 ed, pp. 101-103, 151, 769). The 1999 AWWA Handbook notes that three species of cyanobacteria microalgae, also known as blue-green algae, may be toxic (Ch. 2.13). However, other species including *Chlorella* and *Spirulina* are food nutrients, and *Spirulina* is favored due to its filamentous growth which makes it easy to harvest; moreover, its high (50%) carbon content renders it favorable for direct use for fuel when dried. Nutritionally, *Spirulina* is 60% protein, 20% carbohydrate and a rich source of A, B and E vitamins.

As a consequence, better solutions to purification of water, use of available $CO_2$ and growth of useful microalgae biomass continue to be sought.

SUMMARY OF THE INVENTION

The invention provides a process which uses large amounts of $CO_2$ in photosynthesis to grow cyanobacteria microalgae in an enclosed, deep, slow-flowing water system with optimally-balanced nutrients. Artificial light is diffused throughout the cell within which the flow of water is confined and can be continuously or intermittently supplied as discussed hereinafter. Photocatalysis is present throughout to mineralize organic and inorganic compounds for absorption by the algae and functions synergistically with the microalgae photosynthesis which produces oxygen for use therein. Disinfection costs are reduced when the process is used for tertiary wastewater treatment. Examples of waters to be treated include (1) activated sewage sludge secondary treatment effluent of municipal sewage plants, (2) solubilized farm animal excrement and urine wastes, (3) industrial wastewaters and (4) salt and brackish water. Biomass growth is harvested and dried for fuel or other uses, and with sufficient treatment time, the final effluent is upgraded to potable water. When disposal of $CO_2$ is a primary objective, at least a major portion or all of the water is recycled. In all these processes, biomass growth is harvested and dried for fuel or other uses. In one particular aspect, there is provided a process for improving water quality and growing microalgal biomass, which process comprises the steps of (a) providing at least one cell which is generally closed to liquid flow by ceiling, floor and side walls except for a liquid entrance and an end wall overflow liquid exit, (b) providing partitioning walls in said cell to create an extended flow path of at least about 500 feet total length from said entrance to said exit, (c) coating the surfaces of vertical walls and ceiling with photocatalytic coating material which, in the presence of light of the visible light spectrum of about 400 to 700 nm, will effect mineralization of organic and inorganic compounds so as to provide resulting minerals that are available for absorption by the metabolism of autotrophic cyanobacteria microalgae, (d) supplying a continuous flow of water to be treated to said entrance so that there will be a steady flow of water along the flow path at a velocity of at least about 0.023 feet/second, which flowing water contains autotrophic cyanobacteria microalgae that require $CO_2$ for growth and also contains nutrients to nourish the microalgae, (e) providing $CO_2$ in the flowing water within said cell adequate for microalgae growth, (f) distributing light which covers the visible light spectrum into the flowing water along said flow path from floor to ceiling throughout the cell along the extended flow path, (g) providing ceiling service openings in the cell at spaced locations along said flow path and recovering offgases and harvesting microalgal biomass through said service openings, (h) maintaining the cell water level at a predetermined depth to assure there is void head space between the water surface and said ceiling, and (i) removing water of improved water quality from the cell.

In another particular aspect, the invention provides a process for utilizing $CO_2$ and growing microalgal biomass, which process comprises the steps of (a) providing at least one cell having a floor, a ceiling and side walls, which cell is generally closed to liquid flow except for a liquid entrance and a liquid exit, (b) providing partitioning walls in said cell to create an extended flow path of at least about 500 feet total length from said entrance to said exit, (c) coating the vertical surfaces of said sidewalls and the ceiling surface with photocatalytic coating material which, in the presence of light of the visible light spectrum of about 400 to 700 nm, will effect mineralization of organic and inorganic compounds so as to provide resulting minerals that are available for absorption by the metabolism of autotrophic cyanobacteria microalgae, (d) supplying a continuous flow of water to said entrance so that there will be a steady flow of water along the flow path at a velocity of at least about 0.023 feet/second, which flowing water contains autotrophic cyanobacteria microalgae that require $CO_2$ for growth and also contains nutrients to nourish the microalgae, (e) providing $CO_2$ in the flowing water within said cell adequate for microalgae growth, (f) increasing the amount of surface area in said cell coated with photocatalytic material by locating flat panels in the water in said cell at spaced locations within each channel and aligned parallel to said partitioning walls, (g) distributing light which covers the visible light spectrum into the flowing water from about floor to ceiling throughout the cell along the extended flow path, (h) recovering offgases and harvesting microalgal biomass at spaced locations along said flow path, and (i) removing water through said exit and optionally recycling at least a portion of said water that is removed to said entrance.

In a further particular aspect, the invention provides a process for utilizing $CO_2$ and growing microalgal biomass, which process comprises the steps of (a) providing at least one cell having a floor, a ceiling and side walls, which cell is generally closed to liquid flow except for a liquid entrance and a liquid exit, (b) providing partitioning walls in the cell to create an extended flow path of at least about 500 feet total length from the entrance to the exit, (c) coating the vertical surfaces of the sidewalls and the ceiling surface with photocatalytic coating material which, in the presence of light of the visible light spectrum of about 400 to 700 nm, will effect mineralization of organic and inorganic compounds so as to provide resulting minerals that are available for absorption by the metabolism of autotrophic cyanobacteria microalgae, (d) supplying a continuous flow of water to the entrance so that there will be a steady flow of water along the flow path at a velocity of at least about 0.023 feet/second, which flowing water contains autotrophic cyanobacteria microalgae that require $CO_2$ for growth and also contains nutrients to nourish the microalgae, (e) diffusing $CO_2$ into the flowing water at multiple, spaced locations along the flow path within the cell adequate for microalgae growth so as to maintain an average of at least about 1,000 ppm of $CO_2$ within said flowing water, (f) distributing light which covers the visible light spectrum into the flowing water from about floor to ceiling throughout the cell along the extended flow path, (g) recovering offgases and harvesting microalgal biomass at spaced locations along said flow path, and (h) removing water through the exit and returning at least a major portion of the removed water to the entrance for another pass through the cell, whereby large quantities of $CO_2$ can be efficiently utilized to generate useful biomass.

BRIEF DESCRIPTION OF THE DRAWINGS

FIG. 3 is a fragmentary cross sectional view, enlarged in size, taken generally along line 3-3 of FIG. 1.

DETAILED DESCRIPTION OF THE PREFERRED EMBODIMENTS

To practically employ the process of this invention, an entire waterflow is treated in a closed environment to effect the absorption of all originally contained nutrients (along with supplemental nutrients that are supplied when deficient), and dissolution and mineralization of all organic and inorganic chemical compounds is concurrently accomplished. The range of wastewaters that may be treated covers complex secondary activated municipal sewage laden with nutrients and pollutants at one extreme, and at the other extreme, ocean saltwater containing about 3.5% mineral salts but which is otherwise of relatively good purity, as well as brackish water. To accomplish such objectives, this invention provides a very flexible and adaptable system wherein a treatment process can function effectively in the presence of a wide range of aerobic, anaerobic and autotrophic micro-organisms including problematic bacteria and viruses.

Figure 1:
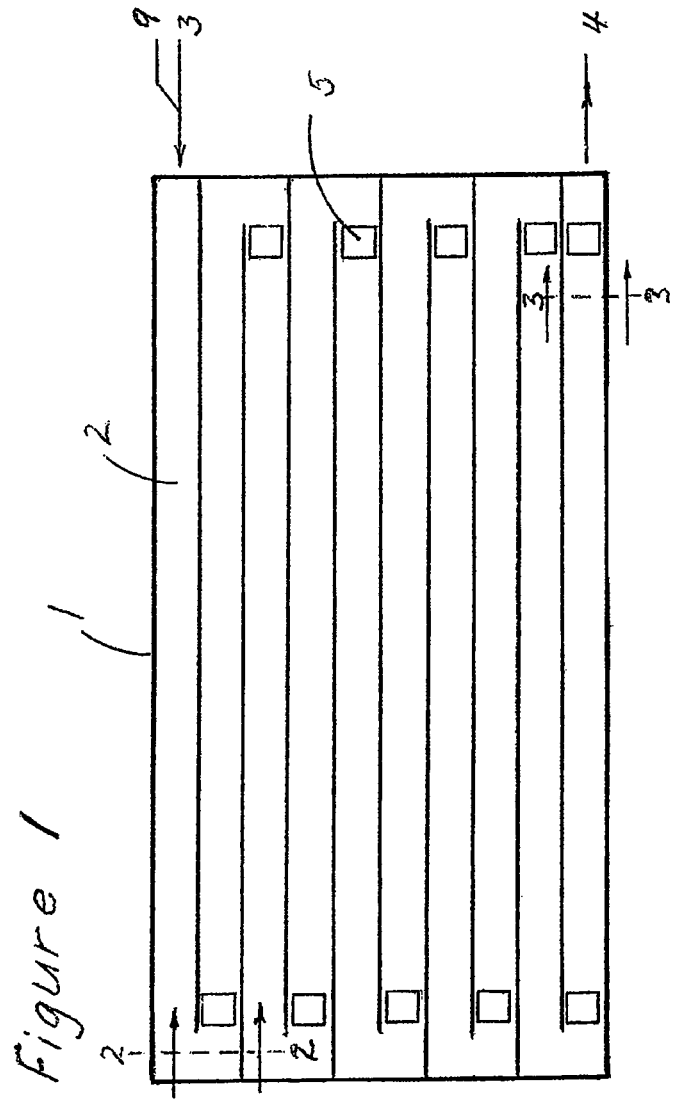
FIG. 1 is a schematic top view of a water treatment cell, channeled for continuous flow, that would generally be arranged as one of a series of such cells, which is depicted with the ceiling removed except for the ten removal devices.

This invention effectively purifies virtually all types of waters by simultaneously employing photosynthesis and photocatalysis which operate synergistically throughout the process. The waterflow is supplied with sufficient $CO_2$ and nutrients for the growth of selected species of cyanobacteria microalgae, such as *Spirulina*, which require $CO_2$ for growth. The growth of cyanobacteria microalgae in this system, by the algae absorption of carbon from $CO_2$, releases the oxygen into the water, benefiting photocatalysis. The waterflow is confined within a closed cell that is well lighted over the visible light spectrum (about 400 to 700 nm) from top to the bottom of a deep, slow-moving waterflow. The process is expected to be most applicable to situations where there will be waterflows of greater than 1,000,000 gallons a day, where such minimum amount might be accommodated in a single closed cell; however, multiple cells are likely used in series to accommodate greater daily flows. In such situations and where there is more than 100 tons of $CO_2$ available per 24 hours, preferred economies of scale can be achieved. The process is also valuable where disposal of $CO_2$ is a primary objective, e.g. from cement or fertilizer manufacture, wherein just about any water source may be used which is then substantially completely recycled. Water flow rates are expected to be maintained within a range of between 0.023 feet per second (f/s), i.e. 0.016 miles per hour (mi/hr) and about 3 f/s; however, flow velocity is preferably limited to about 1.667 f/s, i.e. 1.136 mi/hr and below A water treatment cell is shown in FIG. 1 to exemplify the proportions envisioned for practical scaling. The cell may be constructed of reinforced concrete, partitioned into channels, with about one-foot wall thicknesses and a concrete floor and ceiling. The channels created by the partitions guide the water flow along a serpentine path through the cell, and the channels may be between about 5 feet and about 15 feet wide, with about 10 feet in width being preferred. The cell may have an interior height of between about 5 and 25 feet; however, a height of at least about 10 feet is preferred. A water depth of at least about 6 feet is preferred. However, a water level of at least about 8 feet is more preferably maintained in a cell about 10 feet in height, and such is accomplished by locating an overflow wall as a weir at the exit from the cell to a height of about 8 feet above the floor of the cell. The water depth is so limited to assure some void head space within the generally closed cell. Such head space is preferably maintained to protect ceiling-mounted electric lighting fixtures and wiring from direct water contact and to allow photocatalytic action upon offgases.

From the standpoint of economic feasibility, it is felt that an appropriate cell should have a flow path of at least about 500 feet from entrance to exit, but it is expected to generally be much longer. Generally, it is expected that multiple cells in a series will be used, and water may be pumped or otherwise be caused to flow to succeeding cells in a series of such interconnected cells. Cells having dimensions of about 100 by 200 feet can be constructed two per acre, and if each cell embodies ten channels, the serpentine water flow treatment flowpath will be about 2,000 feet per cell. Filled to a depth of 8 feet, the water capacity of one such cell will be about 1,200,000 gallons. Even small plants may require several cells in a series, and large plants may employ multiple series of such cells. The more complex and dense the total dissolved solids (TDS) in the water flow, the greater is the treatment time required for purification. Total treatment times may vary between 6 and 8 hours for purification of salt water to between 48 and 72 hours for some more complex secondary treatment municipal sewage effluents. It is proposed that a reasonable water quality target for the process of this invention should be about 100 parts per million (ppm) or better for all TDS and minerals content, while toxins and regulated substances, viruses, bacteria, etc., should be destroyed or reduced to levels well below regulatory thresholds. A separate disinfection step is generally practiced in sewage treatment (see AWWA Handbook, 1999: Disinfection, Ch 14.1-60); however, the concurrent processes of photocatalysis and photosynthesis carried out within such a cell are expected to completely disinfect sewage when subjected to optimal time of treatment. Thus, it is expected that effluent can be provided that will be potable and consumer-ready except for final chlorination and fluoridation; however, when purifying some wastewaters a final filtration step may be needed.

Conditioning large masses of water within this cell requires that available light, for both algal biogrowth and photocatalysis, be distributed throughout the interconnected channels within the cell. Recognizing that all of the water will be slowly and continuously in motion flowing along the channels, floor-to-ceiling lighting is preferably incorporated generally uniformly along the entire flowpath. Any suitable lighting devices that provide light in the visible spectrum (about 400 to 700 nm) may be used. Examples of such types of lighting include: (1) bundles of acrylic cord which will depend vertically from a ceiling light source and scatter light along their entire lengths, (2) eight-foot tubular fluorescent lights suspended from ceiling mountings, and (3) floor-to-ceiling LED lights that are likewise vertically suspended in the water being treated. LEDs are presently preferred based on relative efficiency.

It has been found that light/dark periods may accelerate certain microalgae growth. U.S. Pat. No. 3,955,318 to Hulls (1976) cites a beneficial biomass growth rate effect of alternate periods of light (e.g., ½ second to ten seconds) and darkness (e.g. about ten times as long as the light period). Such alternating light and dark periods while frequently harvesting the algae product may well accelerate the growth rate of certain algae and obtain biomass production at a very high level. That patent lists several species of cyanobacteria to which this principle may be applicable (see col. 2 line 65 to col. 3 line 17) including unicellular algae, such as *Chlorella*, and filamentous algae like *Spirulina*. Although these cyanobacteria are preferred, and the species *Spirulina* is particularly preferred, other such suitable cyanobacteria may also be present in the process of the invention. In fact, hundreds of cyanobacteria microalgae species have been identified since 1976, and although it is not yet known how effective this light-to-dark growth enhancement principle might be when applied in practice at large scale, many of these are expected to be suitable for use in these processes.

Assuming that a significant growth rate increase can be gained by constantly alternating artificial light and dark conditions, two such methods may be used in this process: 1) a lights on/off control which continuously cycles light/dark periods within the entire cell, or 2) positioning floor-to-ceiling lights far enough apart within the individual channels to create a short, bright, light period followed by a long dark period (between adjacent light fixtures) as the algae-seeded water slowly and continuously flows along the extended serpentine flow path. The full brightness of light in water such as will be treated in such a cell attenuates rapidly a foot or so from the source; thus, if lights are spaced three to six feet or more apart in a fairly murky water flow, such light/dark period differentials can be achieved without switching lights off and on.

One embodiment of an installation embodying features useful in carrying out the present invention is shown in FIG. 1 where a water treatment cell 1 is schematically illustrated which incorporates an extended, serpentine continuous water flow path comprising ten interconnected channels 2. Water flows into or is pumped into the cell at an entrance 3. One example of possible construction of such a cell 1 for processing and treating wastewater or the like is shown schematically in some detail in FIG. 2. The cell might comprise a concrete basin having a floor or bottom 12, perhaps 1-foot thick, with dimensions 100 feet by 200 feet. Four concrete walls 13 would extend upward from the floor 12 to complete the rectangular basin about 10 feet in interior height. A concrete ceiling 10 might be suitably provided to cover the complete top of the basin, leaving the only liquid flowpath openings at the entrance 3 and the exit 4; the outflow wall at the exit would operate as a weir to maintain the liquid level within the tank at about 8 feet depth of water, leaving about 2 feet of head space below the ceiling 10 that is supported by the 10-foot high sidewalls 13. The interior of the basin is divided by nine partitions 14 which may extend floor-to-ceiling to provide ceiling support, and which create ten channels 2 which each may, for example, be about 10 feet in width (FIGS. 2 and 3 not being drawn specifically to scale). $CO_2$ is supplied by diffusers 7 located centrally of each channel near the floor.

Figure 2:
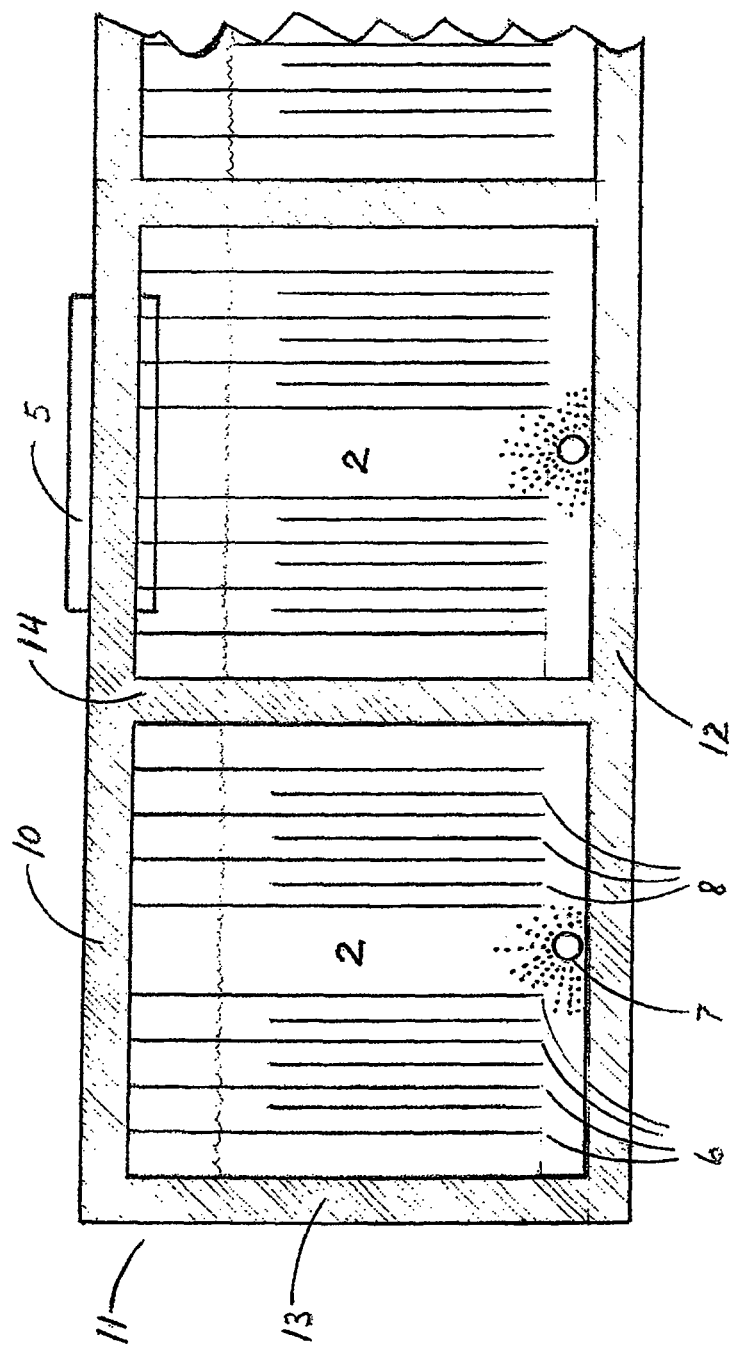
FIG. 2 is a fragmentary cross sectional view, enlarged in size, taken generally along line 2-2 of FIG. 1.

Lighting is illustrated in FIG. 2 as being provided by ceiling-mounted fixtures 6 which distribute light to bundles of acrylic fibers which are spread out and extend essentially from ceiling to floor. Alternatively, ceiling-mounted fluorescent lights of at least 8 feet in length may be vertically suspended to reach within 2 feet of the floor; or strings of LED lights may be ceiling mounted so as to depend vertically therefrom, extending nearly to the floor 12.

At ten spaced locations, preferably generally near one end of each longitudinal channel (which might extend for 200 feet in length), a service opening and removal device 5 is provided to facilitate the removal of microalgae biomass from the surface and the region just below the surface of the water flowing in the cell and to remove and recover offgases. Such offgases may be recycled by addition to the $CO_2$ being fed to the cells through the diffusers 7.

Generally, when such vertically depending lights are used, they may be positioned at regular intervals to provide visible light that nearly completely covers the channels within the cell when it is desired to provide continuous visible spectrum lighting throughout the cell. Such can also be used when it is desired to use an off-on arrangement to create alternating periods of the total light and darkness within the cell to enhance the growth rate of particular microalgae being present within the cell for this treatment process. On the other hand, by spacing the vertical lights at appropriate distances apart along the flowpath, based upon the murkiness of the water being treated and the velocity of the water flow longitudinally in the channel, an arrangement can be created whereby the bacteria and other microorganisms will repeatedly be effectively subjected to alternating periods of visible light followed by substantial darkness, should such an arrangement be desired.

Photocatalysis is an important and integral element of this treatment process and functions synergistically with the microalgae photosynthesis. All interior cell surfaces except the floor are coated with effective photoactive catalysts, i.e. photocatalysts. Photocatalysts are essentially semiconductors in which, when exposed to light, electron-hole pairs develop that generate highly reactive free radicals on the materials surface. Titanium dioxide is one semiconductor of this kind that is capable of removing natural and artificial contaminants in air and water with light exposure so that atmospheric and dissolved oxygen is chemically reduced and the contaminants in the water are oxidized (mineralized) into environmentally friendly end products. An example of one that may be used is the Kronos International carbon-doped $TiO_2$ product that is described in detail in U.S. Pat. No. 7,615, 512 and is effective when exposed to visible light. Such a carbon-doped $TiO_2$ photocatalyst is advantageous because it has self-cleaning properties, and as a result, the interior photoactive surfaces of the cell may need little or no cleaning or resurfacing throughout long periods of continuous waterflow operations. Other photocatalytic coatings which are also active in the visible light range, as known in this art, may also be used; however, $TiO_2$-based coatings and particularly carbon-doped $TiO_2$ coatings are presently preferred.

The preferably about 10 foot deep cell 1 is filled with water being treated to a depth of about 8 feet, which level is controlled by the barrier overflow wall 4 constructed to a height of 8 feet. Carbon dioxide is pumped through the diffuser ducts or piping 7 located as shown at about floor-level extending along the center of the floor of each channel. Depending upon the width of the channels, two or more such diffuser ducts may be located at spaced parallel locations along each channel to ensure continuous and substantially uniform diffusion of $CO_2$ into the slow-flowing water. The gas being diffused should preferably be at least about 95% $CO_2$. Sufficient diffused $CO_2$ is supplied to the water flow within the cell to maintain a presence of at least about 1,000 ppm $CO_2$ and preferably an amount of between about 5,000 and 25,000 ppm. The incoming water flow is monitored, and if it is determined that there are not sufficient nutrients already in the water being treated, nutrients are supplied to the inflow at the entrance 3 through a feeder 9. It is desired to optimize the growth rate of the cyanobacteria microalgae while also removing the dissolved and suspended minerals in the aqueous inflow stream being treated, so excess nutrient addition is avoided when wastewater is being treated. Suitable nutrients, for supply to a wastewater or seawater inflow stream by the feeder 9, are well known in this art for growing microalgal biomass.

Likewise, should the desired strains of cyanobacteria microalgae not already be present in the water inflow to be treated, as for example when salt water or industrial waste is being treated, or when the disposal of $CO_2$ from a cement manufacturer or the like is the primary objective, such can also be introduced through the feeder 9 at the entrance 3, or at some point prior to the cell inflow entrance 3. Cyanobacteria microalgae will grow and multiply readily in such a slow-flowing environment, in the presence of properly balanced nutrients, sufficient $CO_2$ and adequate lighting. As discussed hereinafter, some of the outflow effluent from at least the first cell in a series is preferably recycled to supply viable quantities of microbes which continue and perpetuate the microalgae in the cell. The amount of microalgal biomass harvested will depend somewhat upon the character of the inflow stream; however, for an average wastewater stream of effluent from an activated sludge secondary treatment plant, a cell such as that illustrated containing about 1,200,000 gallons of water, wherein there are appropriate levels of cyanobacteria, nutrients, $CO_2$ and lighting, should produce at least about 10 pounds (dry weight) of microalgal biomass per 24 hour day for each 1,000 gallons of liquid within the cell, and very likely considerably greater amounts will be harvested. Should cell levels fall below this target, additional nutrients and/or $CO_2$ may be supplied. Spaced apart ceiling service openings 5 are equipped with seine or filtration means, to continuously extract algae, for example *Spirulina*, which float to the surface and are present there and in the region immediately therebelow. The ceiling service openings 5 also accumulate offgases which are largely oxygen and carbon dioxide, that are beneficially recycled through the diffuser ducts 7 to enhance algae growth. Alternatively, the offgases may be supplied to an $O_2/CO_2$ condensing boiler combustion system to reduce costs. Any detritus accumulation is removed from the cell floor 12 in periodic cleaning. The water outflow point or exit 4 will usually be connected to the next cell 1 in a series. The last cell in such a series may deliver water to a final filter if needed.

Effective photocatalysis assures breakup of all or most organic and inorganic compounds so that the minerals will be absorbed by the metabolism of algae which require $CO_2$ for growth in photosynthesis, which in turn produces oxygen for use in the photocatalysis. To assure that desired levels of photocatalysis are achieved in the cell 1, it may be desirable to provide coated surface area in addition to the structural walls and the ceiling. Cell channels 2 may include suspended plastic or metal intermediate panels 8 as shown in FIGS. 2 and 3, the vertical surfaces of which are coated with a similar photocatalyst. Such flat panels 8 may be suitably supported from the ceiling, the floor, the side or end walls or the partitions, and they may be positioned about three inches to one foot from adjacent vertically aligned lights to maximize the desired photocatalytic effect that will be obtained. Panels 8 of any convenient size may be used; for example, panels about 6-7 feet high and 1-3 feet wide might be located, parallel to the partitions, in staggered relationship along the length of each channel 2. Generally, sufficient of these panels 8 are provided to increase the photocatalytically coated, vertical wall surface area by at least about 50%; preferably sufficient panels are provided to achieve an increase of at least about 100% and more preferably, at least about 125%.

As mentioned above, it is contemplated that these cells, which may be in the form of large concrete basins, which may be constructed in-ground, above ground, or partially in the ground, will economically be of reasonably large size, for example 100 feet by 200 feet and some 10 feet deep, and might be linked together, e.g. two cells per acre of land. Likewise, it is expected that two or more cells will be linked in series in order to accommodate large flows of wastewater of the like, and large facilities may include multiples of such series of interconnected cells. Similar to secondary wastewater treatment using the activated sludge process, it is likely preferred that a certain portion of the exit flow of at least the first cell within an interconnected series of such cells, is recycled by being returned to the entrance. Preferably, at least about 0.25% of the outflow is recycled, and more preferably up to about 1% is recycled. Because the cyanobacteria microalgae grow profusely on the nutrients in the water being treated, such recycling of the water exiting from an operating cell in a series will assure that the desired cyanobacteria microalgae will be present in at least a desired minimum amount, such as between about one ounce to one pound per 1,000 gallons, on the average, for the water slowly flowing within the cell. Most of the outflow from the final flow in a series of cells for a water treatment process should be potable water. Additional cultured cyanobacteria may be periodically added should testing indicate levels within a cell are approaching a minimum level. Frequent monitoring of the amount of nutrients in the inflow stream will determine when additional nutrients are to be added, through the feeder 9, to the incoming water flow being treated to assure optimum conditions are maintained within the cell.

Although the invention has been described with respect to the best mode presently contemplated by the inventor carrying out this invention, it should be understood that various changes as would be obvious to one ordinarily skilled in this art may be made without departing from the scope of this invention, which is defined in the claims appended hereto.

For example, when salt water, e.g. brackish water or sea water, is being treated wherein some of the minerals present will be photocatalytically oxidized to products that can be readily metabolized by autotrophic microalgae, or when an industrial or agricultural waste stream is being treated, it will often be necessary to add such microalgae to the entering stream by addition thereto and/or recycling. If the objective is $CO_2$ disposal from a Portland cement manufacturer or the like, levels of $CO_2$ of at least about 5,000 ppm may be maintained in the slowly flowing stream, and all or at least a major portion of the exit stream from the cell would then be returned to the entrance where nutrients would be added for another pass therethrough. Biomass would be continuously harvested at the removal locations 5, and once a suitable microalgae population builds up, it will likely be maintained with little additions so long as nutrients are provided. Appropriate nutrients for such autotrophic microalgae are well known in this art and are easily obtained from a wide variety of commercial sources.

Particular features of the invention are emphasized in the claims which follow.

The invention claimed is:

1. A process for improving water quality and growing microalgal biomass, which process comprises the steps of:
    (a) providing at least one cell which is generally closed to liquid flow by ceiling, floor and sidewalls except for a liquid entrance and an end wall overflow liquid exit,
    (b) providing partitioning walls in said cell to create channels that form an extended flow path of at least about 500 feet total length from the entrance to the exit,
    (c) coating the surfaces of the sidewalls and the partitioning walls with photocatalytic coating material that is effective in the presence of light of the visible light spectrum of about 400 to 700 nm to mineralize organic and inorganic compounds in an aqueous stream so as to provide resulting minerals that are available for absorption by the metabolism of autotrophic cyanobacteria microalgae, (d) supplying a continuous stream of water to be treated to the cell entrance to create a steady flow of water along the extended flow path at a velocity of at least about 0.023 feet/second, which flowing water stream contains autotrophic cyanobacteria microalgae that require $CO_2$ for growth and also contains nutrients to nourish the microalgae, (e) injecting $CO_2$ in the flowing water stream within said cell in an amount adequate for microalgae growth, (f) distributing light which covers only the visible light spectrum of about 400 to 700 nm into the flowing water stream from floor to ceiling throughout the cell along the extended flow path, (g) providing ceiling service openings in the cell at spaced locations along the extended flow path and recovering offgases and harvesting microalgal biomass through said service openings, (h) maintaining the cell water level at a depth so as to assure there is void head space between the water surface and the ceiling, and (i) removing water of improved water quality from the cell exit.

2. The process of claim 1 wherein at least about 0.25% of the exit flow is recycled to said entrance to the cell.

3. The process of claim 1 wherein said $CO_2$ is injected by diffusing $CO_2$ into the flowing aqueous stream at multiple locations along the extended flow path.

4. The process of claim 1 wherein multiples of said cells are connected in one or more series to purify large quantities of water.

5. The process of claim 1 wherein the amount of surface area coated with photocatalytic material is increased by locating flat panels in the water flow path in the cell at spaced locations within each channel, which panels are aligned parallel to the partitioning walls.

6. The process of claim 5 wherein the ceiling is coated with photocatalytic material and sufficient of the coated flat panels are provided to increase the total amount of photocatalytically coated surface area over that of the sidewalls and partitioning walls by at least about 50%.

7. The process of claim 1 wherein water flow within the cell is maintained at between about 0.023 feet/second and about 3 feet/second.

8. The process of claim 1 wherein the photocatalytic material is a carbon-doped $TiO_2$.

9. The process of claim 8 wherein sufficient $CO_2$, cyanobacteria microalgae of the species Spirulina, nutrients and light are maintained in said cell to grow and harvest at least about 10 lbs (dry weight) of biomass per day for each 1000 gallons of water in the cell.

10. The process of claim 1 wherein gas containing at least about 95 vol % $CO_2$ is supplied to water flow in an amount sufficient to provide between about 1,000 ppm and about 25,000 ppm of $CO_2$ in the flowing water stream in the cell.

11. The process of claim 1 wherein said visible spectrum light is provided from ceiling-mounted fixtures that support lights that depend vertically downward at spaced locations along each channel.

12. The process of claim 11 wherein said vertically depending lights are submerged in the water to a depth to within about 2 feet or less from the floor.

13. The process of claim 1 wherein the cell partitions form a continuous channel about 5 to 15 feet wide having a height, floor-to-ceiling, of about 5 to 25 feet and wherein the water is maintained at a level to provide a continuous void head space of at least about 2 feet.

14. The process of claim 13 wherein said cell is a concrete rectangular chamber at least 50 feet on each side and wherein the water depth is at least about 6 feet.

15. The process of claim 1 wherein said light distribution is controlled so that said cyanobacteria microalgae in the flowing water stream is exposed to alternating periods of light and dark along the extended flow path to promote a greater algae growth rate.

16. A process for improving water quality wherein microalgal biomass is grown and harvested, which process comprises the steps of:

(a) providing at least one cell having a floor, a ceiling and sidewalls, which cell is generally closed to liquid flow except for a liquid entrance and a liquid exit, (b) providing partitioning walls in the cell to create channels that form an extended flow path of at least about 500 feet total length from the entrance to the exit, (c) coating vertical surfaces of said sidewalls and the partitioning walls with material that is active as a photocatalyst in the presence of light of the visible light spectrum of about 400 to 700 nm to effectively mineralize the nutrient materials and provide resultant minerals that are then available for absorption by the metabolism of cyanobacteria microalgae, (d) supplying a continuous stream of water to be treated to said entrance so that there will be a steady flow of water along the extended flow path at a velocity of at least about 0.023 feet/second, which flowing water contains autotrophic cyanobacteria microalgae that require $CO_2$ for growth and also contains materials to provide nutrients, (e) injecting $CO_2$ into the flowing water stream within said cell in an amount adequate for cyanobacteria microalgae growth, (f) distributing light which covers only the visible light spectrum throughout the flowing water stream along the extended flow path to effectively photocatalytically mineralize the materials in the flowing water and provide resultant minerals that are then available for absorption by the metabolism of the cyanobacteria microalgae, (g) harvesting microalgal biomass at spaced locations along said flow path, and (h) removing water of improved quality through said exit and optionally recycling a portion of said water that is removed to said entrance.

17. The process of claim 16 wherein flat panels which are also coated with the photocatalytic material are located in the water in said cell, at spaced locations within each channel, and aligned parallel to said partitioning walls, which panels have a total surface area equal to at least about 50% of the surface area of photocatalytically coated walls in the cell and wherein sufficient cyanobacteria microalgae of the species Spirulina, $CO_2$, nutrients and light are maintained in the cell to grow and harvest at least about 10 lb (dry weight) of biomass per day per each 1,000 gallons of water in the cell.

18. The process of claim 17 wherein gas containing at least about 95 vol % $CO_2$ is diffused into said flowing water stream at multiple, spaced locations in the cell in an amount sufficient to provide between about 1,000 ppm and about 25,000 ppm of $CO_2$ in the flowing water stream.

19. A process for improving water quality and growing microalgal biomass, which process comprises the steps of:

(a) providing at least one cell having a floor, a ceiling and substantially vertical sidewalls, which cell is generally closed to liquid flow except for a liquid entrance and a liquid exit, (b) providing substantially vertical partitioning walls in the cell to create a channel and form an extended flow path of at least about 500 feet total length from the entrance to the exit, (c) coating the surfaces of the sidewalls and the partitioning walls with material which is active as a photocatalyst in the presence of light of the visible light spectrum of about 400 to 700 nm, (d) supplying a continuous stream of water to be treated to the entrance so that there will be a steady flow of water along the extended flow path at a velocity of at least about 0.023 feet/second, which flowing water stream contains autotrophic cyanobacteria microalgae that require $CO_2$ for growth and also contains materials to provide nutrients for the cyanobacteria microalgae, (e) injecting $CO_2$ into the flowing water at multiple, spaced locations along the extended flow path within the cell so as to maintain an average of at least about 1,000 ppm of $CO_2$ within said flowing water stream, (f) distributing light which covers the visible light spectrum of about 400 to 700 nm into the flowing water stream from about floor to ceiling throughout the cell along the extended flow path to effectively photocatalytically mineralize the nutrient materials so as to provide resultant minerals that are available for absorption by the metabolism of the cyanobacteria microalgae, (g) harvesting microalgal biomass at spaced locations along said flow path, and (h) removing water of improved quality through the exit whereby, as a result of which steps, large quantities of $CO_2$ are efficiently utilized to generate useful biomass.

20. The process of claim 19 wherein sufficient flat panels having vertical surfaces coated with photocatalytic material which is a carbon-doped $TiO_2$ are disposed in the water in the cell, at spaced locations within each channel and aligned parallel to the partitioning walls, to increase the total amount of photocatalytically coated surface area by at least about 50%, and wherein sufficient cyanobacteria microalgae, $CO_2$, nutrients and light are maintained in the cell to grow and harvest at least about 10 lb (dry weight) of biomass per day per each 1,000 gallons of liquid in the cell.

\* \* \* \* \*